United States Patent [19]

Acloque et al.

[11] 4,301,092

[45] Nov. 17, 1981

[54] PREPARATION OF OXALYL CHLORIDE

[75] Inventors: Andre Acloque; Jean-Claude Lanet, both of Saint-Auban; Yves Correia, Chateau Arnoux, all of France

[73] Assignee: Rhone-Poulenc Industries, Paris, France

[21] Appl. No.: 85,104

[22] Filed: Oct. 15, 1979

Related U.S. Application Data

[63] Continuation of Ser. No. 22,055, Mar. 19, 1979, abandoned.

[30] Foreign Application Priority Data

Mar. 17, 1978 [FR] France ............................... 78 07740

[51] Int. Cl.$^3$ ............................................. C07C 51/58
[52] U.S. Cl. ................. 260/544 Y; 560/230; 204/158 HA
[58] Field of Search .................... 260/544 Y; 560/230; 204/158 HA

[56] References Cited

U.S. PATENT DOCUMENTS 2,816,140  12/1957  Ellingboe et al. .............. 260/544 Y

OTHER PUBLICATIONS

Scattergood et al., J.A.C.S., vol. 72 (1950).

*Primary Examiner*—Bernard Helfin
*Attorney, Agent, or Firm*—Burns, Doane, Swecker & Mathis

[57] ABSTRACT

Oxalyl chloride is prepared by (i) first esterifying ethylene glycol with trichloroacetyl chloride, (ii) next photochemically chlorinating the ester which results from the step (i), i.e., ethylene glycol bis-trichloroacetate, and (iii) then decomposing the tetrachloroethylene glycol bis-trichloroacetate thus formed into the desired oxalyl chloride and trichloroacetyl chloride, said steps (i) and (iii) being conducted in the absence of any reaction solvent, other than the trichloroacetyl chloride, and the chlorination step (ii) being conducted at a temperature of from about 50° to 200° C.

14 Claims, No Drawings

PREPARATION OF OXALYL CHLORIDE

CROSS-REFERENCE TO RELATED APPLICATION

This is a continuation of our copending, commonly assigned application, Ser. No. 22,055, filed Mar. 19, 1979 and now abandoned.

BACKGROUND OF THE INVENTION

1. Field of the Invention

The present invention relates to the preparation of oxalyl chloride, and, more especially, to the preparation of oxalyl chloride via chloroxidation of ethylene glycol.

2. Description of the Prior Art

According to U.S. Pat. No. 2,816,140 oxalyl chloride is prepared by heating an ester of tetrachloroethylene glycol and a carboxylic acid to a temperature between 35° and 135° C., in the presence of a catalyst consisting of activated charcoal or certain derivatives of those elements of Group V A of the Periodic Table [Fisher Periodic Chart—1951] having atomic numbers between 7 and 33, e.g., derivatives such as the tertiary amines, amides. Also, the oxalyl chloride is formed simultaneously with trichloroacetyl chloride by the heating of tetrachloroethylene glycol bis-trichloroacetate in chlorobenzene, in the presence of dimethylformamide as the catalyst, at a temperature between 100° and 120° C.

Said '140 patent additionally discloses that the tetrachloroethylene glycol esters utilized in the noted reaction may be obtained by chlorination of the corresponding ethylene glycol esters, such chlorination being performed photochemically employing an excess of chlorine, at a temperature of 75°–125° C., typically in an inert solvent medium, such as carbon tetrachloride.

A process of the aforementioned type has the disadvantage in that it is effected in the presence of solvents [carbon tetrachloride for the chlorination of the ethylene glycol esters, and chlorobenzene for the rearrangement of the tetrachloroethylene glycol esters]; these solvents must then be separated. Further, chlorination in the presence of carbon tetrachloride [boiling point, 77° C.] can be conducted only at low temperatures. Thus, a serious need remains in this art for a process which can be effected in the absence of a solvent medium, and which is susceptible to being carried out over a broad temperature range.

SUMMARY OF THE INVENTION

Accordingly, a major object of the present invention is to provide for the facile preparation of oxalyl chloride, such preparation being devoid of those solvent/temperature limitations which have to date characterized the art.

Briefly according to the invention, oxalyl chloride is prepared by:

(i) First reacting ethylene glycol with trichloroacetyl chloride;

(ii) Photochemically chlorinating the ethylene glycol bistrichloroacetate resulting from the step (i); and thence (iii) Rearranging, or decomposing, the resultant tetrachloroethylene glycol bis-trichloroacetate into the desired oxalyl chloride and trichloroacetyl chloride, said process being characterized in that [1] the steps (i) and (iii), and optionally the step (ii), are conducted in the absence of any solvent, other than the trichloroacetyl chloride, and in that [2] the chlorination reaction is effected at a temperature in the range of between about 50° and 200° C., preferably between about 80° and 160° C.

DESCRIPTION OF THE PREFERRED EMBODIMENTS

The process according to the invention makes use of the following three reactions:

More particularly according to the invention, the aforementioned seriatim process can be represented as follows:

(i) $2\ CCl_3COCl + HOCH_2-CH_2OH \rightarrow Cl_3CCOOCH_2-CH_2OOC\ CCl_3 + 2HCl$ 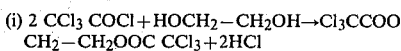

(ii) $Cl_3CCOOCH_2-CH_2OOCCCl_3 + 4\ Cl_2 \rightarrow Cl_3CCOO\ CCl_2-CCl_2OOC\ CCl_3 + 4\ HCl$ 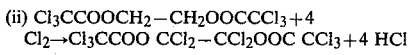

(iii) $Cl_3CCOO\ CCl_2-CCl_2OOC\ CCl_3 \rightarrow 2\ Cl_3CCOCl + ClCO-COCl$ 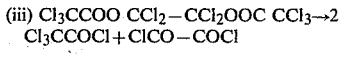

and overall:

$$HOCH_2=CH_2OH + 4\ Cl_2 \rightarrow ClCO-COCl$$ 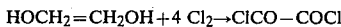

The overall reaction thus is tantamount to a chloroxidation of ethylene glycol. For best results, it is preferred to ensure against the presence of metallic salts in the reaction medium, such as the salts of iron, nickel, aluminum, cobalt, and platinum in amounts greater than 1 ppm. To this end, it is preferred to conduct the various reactions in apparatus made of glass, coated steel, or of polymers devoid of metallic fillers.

Accidental contamination of the several reagents with metallic salts is more readily avoided, simply by performing the three sequences of the process in but a single apparatus.

Reaction (i) and the general preparation of esters from acid chlorides and alcohols are described in Scattergood & Hershenson, *J.A.C.S.*, 72, 2808 (1950).

For best results, reaction (i) is conducted in the presence of a 2 to 500% by weight stoichiometric excess of trichloroacetyl chloride, at a temperature between 60° and 80° C. at the beginning of the reaction; subsequently, the temperature is permitted to rise to the reflux temperature of the system.

Reaction (ii) may be carried out utilizing any radiation capable of being absorbed by the chlorine molecule, i.e., any of that radiation having wavelengths between about 200 and 600 nanometers. Exemplary thereof, there are mentioned: low, medium and high pressure mercury vapor lamps being provided with a coating permitting the re-emission of rays having a wavelength capable of being absorbed by chlorine; ordinary filament lamps; the so-called "neon" illuminating devices; etc. For best results according to the invention, the subject reaction is preferably conducted at a pressure between about 500 mm Hg absolute and 5 bars, in the presence of a slight stoichiometric excess of chlorine, on the order of about 1 to 5%, said slight excess being swept away, or purged, by the gaseous hydrochloric acid formed during the course of the reaction.

The chlorine used must be dry, exhibit a purity on the order of 99.8, preferably contain less than 0.1% oxygen and be free of trace amount of metals, particularly iron whether in metallic or salt form.

The reaction (iii) is conducted at a temperature of between about 50° and 160° C., preferably between about 60° and 120° C., in the presence of the trichloroacetyl chloride and of from about 2 to 1000 ppm, preferably 20 to 250 ppm, of suitable catalyst, such as a tertiary amine [triethylamine, pyridine, dimethylaniline, and the like], or the chlorhydrates thereof.

In order to further illustrate the present invention and the advantages thereof, the following specific examples are given, it being understood that same are intended only as illustrative and in nowise limitative.

EXAMPLE 1

The apparatus utilized was a 4 liter glass flask, equipped with means for mechanical agitation, a thermometer, a bromine ampoule, was surmounted by a distillation column and was externally illuminated by a 200 watt lamp.

Into the aforesaid flask, 15 moles of trichloroacetyl chloride were introduced and heated to 80°–100° C. Subsequently, in about two hours, 6 moles of anhydrous ethylene glycol were added thereto.

The hydrochloric acid evolved passed through the distillation column and was absorbed by water. The reaction was continued through reflux while the excess trichloroacetyl chloride was drawn off. An analysis for iron at this stage in the reaction reflected the presence of 0.1 mg/kg iron in the reaction medium.

The flask was then maintained at 130° C. and chlorine was introduced under illumination, such that the hydrochloric acid formed contained approximately 1% by weight of chlorine; in such process, the temperature rose to 160° C. After 8 hours, 30 minutes, a stoichiometric amount of hydrochloric acid was collected.

The reaction medium was cooled by degassing the dissolved chlorine with nitrogen, and the excess trichloroacetyl chloride drawn off during the esterification reaction was added.

To the resulting mixture, at a temperature of about 60° C., 200 mg/kg triethylamine chlorhydrate was added and the temperature was permitted to progressively rise under agitation.

Initially, 618.6 g oxalyl chloride (boiling point = 62° C.), representing a yield of 81% with respect to the glycol converted, were collected.

Subsequently, trichloroacetyl chloride (boiling point = 120° C.) was collected in a yield of 90% and, ultimately, 164 g of a heavier residue (boiling point$_{15}$ = 90°–100° C.) consisting of partially chlorinated glycol bis-(trichloroacetate) were collected.

EXAMPLE 2

This example presents a variation of the process described in Example 1, consisting, after the recovery by means of distillation of the oxalyl chloride formed, of adjusting the amount of the trichloroacetyl chloride present in the flask so as to recover the initial amount of said trichloroacetyl chloride and to proceed to a new experiment without withdrawing the excess trichloroacetyl after rectification; the chlorination then requires 18 to 20 hours.

This variation improved the yield in oxalyl chloride (86% with respect to glycol) without modifying the rate of recovery of the trichloroacetyl chloride (90%).

EXAMPLES 3 to 6

The procedure described in Example 1 was repeated by effecting the chlorination at a temperature of between 120° and 150° C., in the presence of varying amounts of iron, under illumination by means of a medium pressure UV lamp, the rearrangement or decomposition reaction being conducted in the presence of 100 mg/kg triethylamine chlorhydrate.

The results of this procedure are presented in the table which follows:

TABLE

| EXAMPLES | 3 | 4 | 5 | 6 |
|---|---|---|---|---|
| Duration of chlorination, in hours | 32 | 26.5 | 31 | 28 |
| Yield in COCl—COCl | 48.5 | 38.5 | 72 | 84 |
| Yield in Cl$_3$CCOCl | 60 | 55 | 87 | 89 |
| Iron content, mg/kg | ~6 | ~2 | 1 | <<1 |

These experiments demonstrate the detrimental effect of the presence of metallic salts in the reaction medium.

EXAMPLE 7

The apparatus utilized was fabricated from glass and comprised a 4 liter flask, equipped with a mechanical agitator, a thermometer, a bromine ampoule, and was surmounted by a distillation column and externally illuminated by means of a 200 watt lamp. Into the flask, 15 moles of trichloroacetyl chloride were introduced and heated to 80°–100° C.; after two hours, 6 moles of anhydrous ethylene glycol were added.

The hydrochloric acid evolved passed through the distillation column and was absorbed in water; the mixture was then brought to reflux for 1 hour. The temperature was reduced to 80° C. and chlorine gas was introduced under illumination, while permitting the temperature to progressively rise to 120° C.; the escaping HCl contained approximately 1% chlorine. After 18 hours, the amount of HCl evolved corresponded to the theoretical amount. The mixture was then cooled to 60° C. and 500 mg triethylamine chlorhydrate were introduced, while the temperature was permitted to progressively rise; in two hours, reflux was attained and the withdrawal of the oxalyl chloride began.

648 g of oxalyl chloride were recovered; this represented a yield of 85% with respect to the glycol.

The trichloroacetyl chloride formed was not distilled, but was retained in the reaction medium and its volume readjusted (8% loss was found). A new cycle may then be initiated.

EXAMPLE 8

Into a glass reactor having a capacity of 60 liters, equipped with a high pressure mercury lamp and provided with those features described in Example 1, 285 moles of trichloroacetyl chloride were introduced (51.87 kg).

The noted medium was heated to 80°–100° C. and in 3 hours, 52.4 moles (3.249 kg) anhydrous ethylene glycol were introduced.

The hydrochloric acid evolved passed through the distillation column and was absorbed in water.

The reaction was continued through reflux in 2 hours, then the temperature of the reaction mass was reduced to 60° C.; analysis for iron at this stage in the reaction indicated the presence of at least 0.1 mg/kg iron therein. Subsequently, under illumination, excess chlorine was introduced over 24 hours, such that the hydrochloric acid exiting the reactor contained 1 to 2% by weight of chlorine, with the temperature being pogressively raised to 90° C., then 120° C.

The reaction was continued through reflux and the chlorine purged via nitrogen flow upon completion of the reaction.

The reaction medium was cooled to 60°–65° C. and 200 mg/kg triethylamine chlorhydrate were added thereto.

The temperature was pemitted to progressively rise and, by means of distillation, 5.66 kg oxalyl chloride were withdrawn (corresponding to a yield of 85% with respect to the glycol), together with trichloroacetyl chloride, the latter being recovered in a yield of 96%.

EXAMPLE 9

Into an enamelled steel reactor having a capacity of 1500 liters, equipped with liquid inlet agitation means and surmounted by a distillation column, there were introduced 2 T ($11 \times 10^{+3}$ moles) of trichloroacetyl chloride having a purity of 98% and, at 90° C., after approximately 2 hours, 150 kg ($2.42 \times 10^3$ moles) anhydrous ethylene glycol were added. This mixture was then heated to 120° C. in 1 hour. The solution of ethylene glycol bis-trichloroacetate in the trichloroacetyl chloride contained less than 1 ppm iron. The reaction mixture was introduced into a photochlorination reactor having a ratio of illuminated surface/volume of 28 $m^2/m^3$ and which was equipped with a mercury vapor lamp emitting light of wavelength greater than 400 nm. With an initial temperature of approximately 80° C., chlorine gas was introduced thereto such that the hydrochloric acid did not contain more than 1% by volume chlorine at the reactor outlet. After 24 hours of chlorination, with the temperature having been increased from 80° to 110° C. and the mixture exhibiting no characteristic hydrogen band under IR, the chlorination was discontinued; a stream of nitrogen was passed therethrough at 10 $m^3/h$ for ¼ hour to flush out the dissolved chlorine and the reaction medium was then transferred into a glass coated steel reactor having a capacity of 1500 liter, wherein, at 55°–60° C., 100 g triethylene chlorhydrate were added and the temperature permitted to progressively rise over a period of 2 hours, to reflux.

249 kg ($1.96 \times 10^3$ moles) of oxalyl chloride (boiling point = 62'–64° C.) were recovered, representing a yield of 81% with respect to the glycol. The trichloroacetyl chloride was retained for a subsequent operation, after readjustment of its volume.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the preparation of oxalyl chloride comprising:
   (i) esterifying ethylene glycol with trichloroacetyl chloride, in the absence of any reaction solvent other than trichloroacetyl chloride, to afford ethylene glycol bis-trichloroacetate, the reaction mixture for the esterification consisting essentially of ethylene glycol, trichloroacetyl chloride and the reaction products thereof, and the hydrochloric acid produced during the esterification being removed from the reaction mixture by distillation;
   (ii) photochemically chlorinating the resulting ethylene glycol bis-trichloroacetate, at a temperature of from about 50° to 200° C., to afford tetrachloroethylene glycol bis-trichloroacetate;
   (iii) decomposing the resulting tetrachloroethylene glycol bis-trichloroacetate, at a temperature of from about 50° to 160° C., in the presence of trichloroacetyl chloride as the sole reaction solvent, and in the presence of a decomposition catalyst, to afford oxalyl chloride and trichloroacetyl chloride; and
   (iv) separating the resulting oxalyl chloride.

2. The process as defined by claim 1, the chlorination step (ii) being conducted at a temperature of from about 80° to 160° C.

3. The process as defined by claim 1, the reaction medium containing no more than about 1 ppm metallic salts.

4. The process as defined by claim 1, the esterification step (i) being conducted with an about 2 to 500% by weight stoichiometric excess of trichloroacetyl chloride, and at a temperature gradually increasing from 60° to 80° C. to reflux.

5. The process as defined by claim 1, the chlorination step (ii) being conducted in the presence of a 1 to 5% stoichiometric excess of chlorine, and under a pressure of from about 500 nm Hg, absolute, to 5 bars.

6. The process as defined by claim 1, the decomposition catalyst being a tertiary amine, or chlorhydrate thereof, in an amount of from 20 to 250 ppm.

7. The process as defined by claim 6, the decomposition step (iii) being conducted at a temperature of from 60° to 120° C.

8. The process as defined by claim 6, the decomposition catalyst being selected from the group comprising triethylamine, pyridine and dimethylaniline.

9. The process as defined by claim 1, all of the steps (i), (ii) and (iii) being conducted in the same reaction vessel.

10. The process as defined by claim 1, the chlorination step (ii) being conducted in a reaction vessel separate from that in which the steps (i) and (iii) are conducted.

11. The process as defined by claim 9, said reaction vessel being comprised of a member selected from the group comprising glass, steel, and polymer devoid of metallic filler.

12. The process as defined by claim 10, said reaction vessels each being comprised of a member selected from the group comprising glass, steel, and polymer devoid of metallic filler.

13. The process as defined by claim 1, wherein step (ii) is conducted in the absence of any reaction solvent.

14. The process as defined by claim 1, wherein step (ii) is conducted in the presence of trichloroacetyl chloride as the sole reaction solvent.

* * * * *